United States Patent [19]

Schröer et al.

[11] 4,233,233

[45] Nov. 11, 1980

[54] PROCESS FOR THE PREPARATION OF 2-OXOIMINOPHENYLACETONITRILE

[75] Inventors: Horst Schröer, Prairie Village, Kans.; Karl Goliasch, Berg. Gladbach; Uwe Beck, Cologne, both of Fed. Rep. of Germany

[73] Assignee: Bayer Aktiengesellschaft, Leverkusen, Fed. Rep. of Germany

[21] Appl. No.: 35,755

[22] Filed: May 3, 1979

[30] Foreign Application Priority Data

Jun. 10, 1978 [DE] Fed. Rep. of Germany ....... 2825565

[51] Int. Cl.$^3$ ............................................. C07C 121/78
[52] U.S. Cl. ................................................. 260/465 E
[58] Field of Search ........................ 260/465 E, 566 A

[56] References Cited

U.S. PATENT DOCUMENTS

| | | | |
|---|---|---|---|
| 2,749,358 | 6/1956 | Heilly | 260/465 E |
| 3,090,812 | 5/1963 | Witbert et al. | 260/566 A |
| 3,822,314 | 7/1974 | Gay et al. | 260/566 A |

OTHER PUBLICATIONS

Houben–Weyl, Methoden der Organishen Chemie, vol. 10/4, pp. 30–32 (1968).
Stevens, J. Org. Chem., vol. 28, pp. 2436–2438 (1963).
Thurston, et al., J. Org. Chem., vol. 2, pp. 192–193 (1938).

*Primary Examiner*—Dolph H. Torrence
*Attorney, Agent, or Firm*—Sprung, Felfe, Horn, Lynch & Kramer

[57] ABSTRACT

In the preparation of 2-oximinophenylacetonitrile by reacting benzyl cyanide with an alkyl nitrite in the presence of a base, the improvement which comprises employing an inorganic base as the base and effecting the reaction in an aqueous solution of an alcohol. Advantageously the reaction mixture, consisting of an alcohol, an aqueous solution of an inorganic base and benzyl cyanide, is circulated by means of a pump and thereby operates an injector which sucks in the alkyl nitrite. Desirably the alkyl nitrite is a $C_1$–$C_5$ alkyl nitrate having the same alkyl radical as the alcohol, about 1.05 to 1.15 moles of alkyl nitrite are employed per mole of benzyl cyanide, the inorganic alkali is an aqueous solution of potassium hydroxide or sodium hydroxide, the molar ratio of benzyl cyanide to potassium or sodium hydroxide is about 1:1.1–1.3, the reaction is effected at about 20° to 40° C., and after the reaction has ended the alkaline reaction mixture is acidified with hydrochloric acid or sulphuric acid at a temperature above about 40° C. and the 2-oximinophenylacetonitrile formed is separated off.

11 Claims, No Drawings

PROCESS FOR THE PREPARATION OF 2-OXOIMINOPHENYLACETONITRILE

The present invention relates to an unobvious process for the preparation of 2-oximinophenylacetonitrile, which can be used as an intermediate product for the synthesis of pesticidally active compounds.

The preparation of 2-oximinophenylacetonitrile is known. A comprehensive survey of the preparative processes has been published in Houben-Weyl, Methoden der organischen Chemie (Methods of Organic Chemistry), volume X/4 (1968), 4th edition. According to these processes, 2-oximinophenylacetonitrile can be prepared, for example, by reacting benzyl cyanide, an alkyl nitrite and a sodium alcoholate in an anhydrous alcohol (see also T. E. Steven, J. org. Chem. 28, 2436 (1963) and J. T. Thurston, J. org. Chem. 2, 192 (1938)).

The present invention now provides a process for the preparation of 2-oximinophenylacetonitrile by reacting benzyl cyanide with an alkyl nitrite in the presence of a base wherein an alkyl nitrite is metered into a mixture of an alcohol, an aqueous solution of an inorganic base and benzyl cyanide, the solution of the 2-oximinophenylacetonitrile base salt is acidified when the reaction has ended and the 2-oximinophenylacetonitrile is then isolated.

The course of the reaction in the process according to the invention can be represented by the equation which follows:

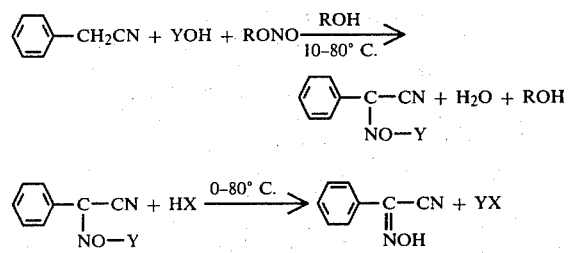

In this equation, Y-OH denotes a strong inorganic base, HX denotes a mineral acid and R denotes an alkyl radical.

It is surprising that instead of an expensive alkali metal alcoholate which is difficult to handle, it is also possible to employ concentrated, aqueous solutions of inorganic bases and a water-containing alcohol, as a solvent, very successfully in the reaction according to the invention.

Various alkyl nitrites can be used in the process according to the invention. The lower homologoes $CH_3ONO$ to $C_5H_{11}ONO$ are preferably used, because of their relatively high rate of reaction.

The molar ratio of benzyl cyanide to alkyl nitrite can be about 1:1 to 1:1.2, preferably about 1:1.05 to 1:1.15.

The alkyl radical of the alcohol employed as the solvent is of no importance for the reaction. However, the alkyl radical preferably corresponds to that of the alkyl nitrite, in order to make later working up of solutions easier.

Possible bases are all the strong, inorganic bases. Aqueous solutions of sodium hydroxide or potassium hydroxide are preferably employed.

If the reaction is carried out with alkali metal hydroxide solution, the molar ratio of benzyl cyanide to alkali metal hydroxide can be about 1:1 to 1:1.5, preferably about 1:1.1 to 1:1.3.

The oximation reaction proceeds exothermically. The reaction in the process according to the invention can be carried out at about 10° to 80° C., preferably between about 20° and 40° C.

The main reaction has ended in the course of a few minutes. It depends on the nature of the alkyl nitrite employed and on the procedure.

Any strong acid can be used for neutralizing the alkaline reaction mixture. Industrial hydrochloric acid or sulphuric acid can preferably be employed. The neutralization can be carried out at temperatures from about 0° to 80° C., preferably between about 40° and 60° C.

After cooling the mixture, after diluting with cold water or after distilling off the alcohol, the oximinophenylacetonitrile crystallizes out and can be isolated by filtration.

The process described makes it possible to prepare 2-oximinophenylacetonitrile without isolating intermediate products.

The reaction can be successfully carried out continuously and discontinuously. A continuous procedure is particularly preferred, according to which the reaction solution, which consists, for example, of methanol, sodium hydroxide solution and benzyl cyanide, is circulated by means of a pump and thereby operates an injector which sucks in, for example, methyl nitrite.

2-Oximinophenylacetonitrile is obtained in high purity and good yield by the process according to the invention. 2-Oximinophenylacetonitrile is suitable for the preparation of valuable phosphoric acid esters, phosphonic acid esters, thionophosphoric acid esters and thionophosphonic acid esters, which can successfully be employed in plant protection for combating harmful sucking and biting insects, Diptera and mites (Acarina), as well as in the veterinary field and hygiene field, and also in protecting stored products from a large number of animal pests (endoparasites and ectoparasites) (see, for example, German Patent Specification No. 1,238,902).

The process of this invention is illustrated in the following examples:

EXAMPLE 1

290 g of methyl nitrite were passed into a solution of 980 g of methanol, 480 g of 50% strength sodium hydroxide solution and 468 g of benzyl cyanide at 40° C. in the course of 3 hours. The mixture was stirred at 40° C. for half an hour and diluted with 7 liters of ice-water. The mixture was adjusted to pH 2.5 with hydrochloric acid. The oximinophenylacetonitrile formed was filtered off and washed with water. Yield: 545 g of 100% pure oximinophenylacetonitrile (about 93.3% of theory).

EXAMPLE 2

105 g of isopropyl nitrite were added to a mixture of 70 g of isopropanol, 130 g of 40% strength sodium hydroxide solution and 114 g of benzyl cyanide at 30° C. in the course of 9 hours.

The mixture was adjusted to pH 2.5 with hydrochloric acid. Excess isopropyl nitrite and isopropanol were distilled off in vacuo. The oximinophenylacetonitrile formed was filtered off at 20° C. and washed with water. Yield: 122 g of 100% pure oximinophenylacetonitrile (about 86% of theory).

EXAMPLE 3

167 g of methyl nitrite were passed into a solution of 475 g of methanol, 215 g of water, 126 g of sodium hydroxide and 279 g of benzyl cyanide at 35° C. in the course of 4.5 hours. The mixture was stirred at 35° C. for half an hour. Hydrochloric acid was added to pH 2.5 and the temperature was allowed to rise to 55° to 60° C.

The mixture was discharged onto 4 liters of ice-water in the course of 0.5 hour. The oximinophenylacetonitrile formed was filtered off and washed with water. Yield: 317 g of 100% pure oximinophenylacetonitrile (about 91% of theory).

EXAMPLE 4

200 kg/hour of methanol, 80 kg/hour of 50% strength sodium hydroxide solution, 60 kg/hour of water and 94 kg/hour of benzyl cyanide were reacted with one another at 35° C. The reaction solution was circulated by means of a pump and an injector, which sucked in 54 kg/hour of methyl nitrite, was thereby operated.

Part of the reaction mixture was removed, according to the rate at which the starting materials were fed in.

The reaction was carried out under normal pressure.

After diluting the reaction mixture with water and acidifying it with sulphuric acid, the oximinophenylacetonitrile formed was filtered off and washed with water. Yield: 103 to 108 kg/hour of oximinophenylacetonitrile (about 88 to 92% of theory).

It will be appreciated that the instant specification and examples are set forth by way of illustration and not limitation, and that various modifications and changes may be made without departing from the spirit and scope of the present invention.

What is claimed is:

1. In the preparation of 2-oximinophenylacetonitrile by reacting benzyl cyanide with an alkyl nitrite in the presence of a base, the improvement which comprises employing an inorganic base as the base, effecting the reaction in an aqueous solution of an alcohol, and after the reaction has ended acidifying the reaction mixture and isolating the 2-oximinophenylacetonitrile therefrom.

2. A process according to claim 1, wherein the reaction is effected by metering the alkyl nitrite into a mixture of the alcohol, an aqueous solution of the inorganic base and the benzyl, cyanide, thereby to form a solution of the 2-oximinophenylacetonitrile base salt.

3. A process according to claim 1, wherein about 1 to 1.2 moles of alkyl nitrite are employed per mole of benzyl cyanide.

4. A process according to claim 1, wherein the inorganic base is an aqueous solution of an alkali metal hydroxide.

5. A process according to claim 4, wherein the molar ratio of benzyl cyanide to alkali metal hydroxide is from about 1:1 to 1:1.5.

6. A process according to claim 1, wherein the alkyl nitrite is a $C_1$–$C_5$-alkyl nitrite.

7. A process according to claim 1, wherein after the reaction has ended, the alkaline reaction mixture is acidified with hydrochloric acid or sulphuric acid at a temperature above about 40° C. and the 2-oximinophenylacetonitrile formed is separated off.

8. A process according to claim 1, wherein the reaction mixture, consisting of an alcohol, an aqueous solution of an inorganic base and benzyl cyanide, is circulated by means of a pump and thereby operates an injector which sucks in the alkyl nitrite.

9. A process according to claim 1, wherein the reaction temperature is from about 10° to 80° C.

10. A process according to claim 1, wherein the alcohol contains the same alkyl radical as the alkyl nitrite.

11. A process according to claim 8, wherein the alkyl nitrite is a $C_1$–$C_5$ alkyl nitrite having the same alkyl radical as the alcohol, about 1.05 to 1.15 moles of alkyl nitrite are employed per mole of benzyl cyanide, the inorganic alkali is an aqueous solution of potassium hydroxide or sodium hydroxide, the molar ratio of benzyl cyanide to potassium or sodium hydroxide is about 1:1.1–1.3, the reaction is effected at about 20° to 40° C., and after the reaction has ended the alkaline reaction mixture is acidified with hydrochloric acid or sulphuric acid at a temperature above about 40° C. and the 2-oximinophenylacetonitrile formed is separated off.

* * * * *

UNITED STATES PATENT AND TRADEMARK OFFICE
CERTIFICATE OF CORRECTION

PATENT NO. : 4,233,233
DATED : Nov. 11, 1980
INVENTOR(S) : Horst Schröder et al

It is certified that error appears in the above-identified patent and that said Letters Patent are hereby corrected as shown below:

Title Page, Inventors   Delete "Schröer" and insert

--Schröder--.

Signed and Sealed this

Twenty-eighth Day of April 1981

[SEAL]

Attest:

RENE D. TEGTMEYER

Attesting Officer   Acting Commissioner of Patents and Trademarks